United States Patent [19]

Baxter et al.

[11] Patent Number: 4,560,687
[45] Date of Patent: Dec. 24, 1985

[54] SUBSTITUTED AROMATIC COMPOUNDS

[76] Inventors: Martin G. Baxter, 34 Whitehead Close, Wilmington, Dartford, Kent; Albert R. Elphick, 51 Baring Rd., Lee, London, S.E. 12; Alistair A. Miller, 91 Elmshurst Gardens, Tonbridge, Kent; David A. Sawyer, 60 Bourne Vale, Hayes, Kent, all of England

[21] Appl. No.: 585,022

[22] Filed: Mar. 5, 1984

Related U.S. Application Data

[60] Continuation of Ser. No. 302,407, Sep. 15, 1981, abandoned, which is a division of Ser. No. 154,199, May 29, 1980, abandoned.

[30] Foreign Application Priority Data

Jun. 1, 1979 [GB] United Kingdom ............... 7919256

[51] Int. Cl.[4] .................. C07D 253/06; A61K 31/53
[52] U.S. Cl. .................................... 514/242; 544/182; 260/465 E
[58] Field of Search ............... 544/182; 424/249; 514/242

[56] References Cited

U.S. PATENT DOCUMENTS

| | | | |
|---|---|---|---|
| 2,952,677 | 9/1960 | Birtwell et al. | 260/240 |
| 3,637,688 | 1/1972 | Rees et al. | 260/465 E X |
| 4,311,701 | 1/1982 | Roth et al. | 424/249 |

FOREIGN PATENT DOCUMENTS

| | | | |
|---|---|---|---|
| 190941 | 9/1956 | Austria . | |
| 1802364 | 5/1969 | Fed. Rep. of Germany . | |
| 511216 | 9/1971 | Switzerland . | |
| 759014 | 10/1956 | United Kingdom | 544/182 |
| 1223491 | 2/1971 | United Kingdom . | |
| 1318645 | 5/1973 | United Kingdom . | |

OTHER PUBLICATIONS

C.A., 48, (1954), Hitchings, et al., 2719i.
C.A., 51, (1957), Burroughs Wellcome, 9719e.
C.A., 53, (1959), Burroughs Wellcome, 7216h.
C.A., 53, (1959), Wellcome Foundation, 13186d.
C.A., 53, (1959), Winzler, et al., 14345h.
C.A., 55, (1961), Beyer, et al., 2676e.
C.A., 65, (1966), Settepani, et al., 52161f.
C.A., 68, (1968), Bhalla, et al., 104123n.
C.A., 74, (1971), Castland, et al. 99946a.
C.A., 76, (1972), Rees, et al., 113258c.
C.A., 77, (1972), Vorbreugger, 48150r.
C.A., 68, (1968). Kittler, et al., 26976b.
C.A., 71, (1969), Heinisch, 49900y.
C.A., 74, (1971), Taylor, et al., 87927g.
C.A., 71, (1969), Hornyak, et al., 70570a.
C.A., 77, (1972), Rees, et al., 122123c.
C.A., 79, (1973), Vorbrueggen, 66405y.
C.A., 85, (1976), March, et al., 180p.
C.A., 85, (1976), Neunhoeffer, et al., 21299z.
C.A., 85, (1976), Piskala, et al., 46598j.
C.A., 85, (1976), Hegarty, et al., 154151s.
C.A., 86, (1977), Wasti, et al., 43661j.
C.A., 86, (1977), Wasti, et al., 171386k.
C.A., 87, (1977), Hegarty, et al., 33694d.
C.A., 87, (1977), Hegarty, et al., 112003f.
C.A., 87, (1977), Berg, et al., 117366m.
C.A., 88, (1978), Neunhoeffer, et al., 121113q.
Rees, et al.; J. of Med. Chem., 15, (1972), pp. 859–861.
Rosenberg, et al.; Proc. Soc. Exp. Biol., (1964), 115, pp. 410–414.
Woodbury, et al.; Arch. Int. Pharmacodyn., (1952), 92, pp. 97–107.

*Primary Examiner*—Joseph Paul Brust
*Attorney, Agent, or Firm*—Donald Brown

[57] ABSTRACT

The present invention provides compounds of the formula (III):

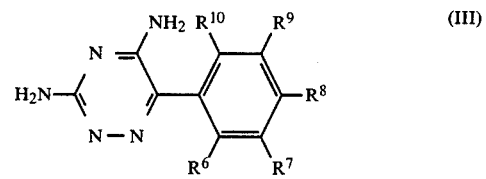

or an acid addition salt thereof, wherein $R^6$, $R^7$, $R^9$ and $R^{10}$ are each hydrogen, halogen, $C_{1-4}$ alkyl or trifluoromethyl and $R^8$ is chlorine or $R^7$ and $R^8$ are linked to form a —CH=CH—CH=CH— group when one of $R^6$ and $R^{10}$ is other than hydrogen provided that when $R^8$ is chlorine $R^6$, $R^7$, $R^9$ and $R^{10}$ are not all hydrogen atoms and that any one of $R^6$, $R^7$, $R^9$ and $R^{10}$ is not chlorine when the other three groups are hydrogen. Also provided are pharmaceutical compositions containing compounds of the formula (III), the first medical use of compounds of the formula (III), a process for preparing such compounds and intermediates through which this process proceeds.

9 Claims, No Drawings

SUBSTITUTED AROMATIC COMPOUNDS

This application is a continuation of application Ser. No. 302,407, filed Sept. 15, 1981, now abandoned, which in turn is a division of application Ser. No. 154,199, filed May 29, 1980, now abandoned.

The present invention relates to a group of novel compounds which are useful in the treatment of CNS disorders, such as epilepsy, to pharmaceutical compositions containing them, and to methods for their preparation.

U.K. Pat. No. 759 014 discloses compounds of the formula (I):

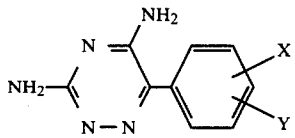

wherein X and Y are hydrogen and halogen atoms, as having activity against bacterial and malarial infections in animals. This patent specifically discloses those compounds wherein X and Y are both hydrogen atoms, wherein X is a hydrogen atom and Y is a 4-chloro atom and wherein X is a 4-chloro atom and Y is a 2-chloro or 3-chloro atom respectively.

Rees et al, *J. Med. Chem.*, 1972 15, 859, have shown that these compounds, and in particular the 4-chlorophenyl, and the 3,4-dichlorophenyl compounds are active against the malaria organism *Plasmadium berghei* in mice. However, these two compounds were also shown to be toxic at curative doses and presumably were not investigated further because of their low therapeutic ratio in this context. The 2,4-dichlorophenyl compound had only slight antimalarial activity. The therapeutic ratio of the compounds were such as to prevent their use in human medicine for the treatment or prophylaxis of malaria and they were not progressed further.

U.S. Pat. No. 3,637,688 discloses compounds of the formula (II):

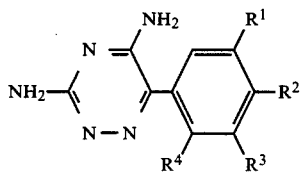

wherein $R^1$ is hydrogen or fluorine, and $R^2$, $R^3$ and $R^4$ are hydrogen, fluorine or trifluoromethyl provided that at least one of $R^1$, $R^2$, $R^3$ and $R^4$ is fluorine or trifluoromethyl, as being useful in the treatment of malaria. In the Rees article referred to above, the 4-trifluoromethylphenyl compound (II; $R^2 = CF_3$, $R^1 = R^3 = R^4 = H$) was claimed to be less toxic than the chlorophenyl compounds whilst still being active against malaria. The other fluoro and trifluoromethyl compounds referred to in the article were substantially less active than the 4-trifluoromethylphenyl compound.

Rosenburg and Bottiroli *Proc. Soc. exp. Biol.*, 1964, 115,410, described a series of tests in which three antimalarial agents, quinacrine, chloroquine and hydroxychloroquine, were tested as anticonvulsants. Only hydroxychloroquine possessed a favourable activity profile.

It has now been discovered that a group of novel 3,5-diamino-6-(substituted phenyl)-1,2,4-triazines are active in the treatment of CNS disorders, such as pyschiatric and neurological disorders, and are particularly useful as anticonvulsants, for example in the treatment of epilepsy. Furthermore, these triazines are believed to be nondepressant at likely therapeutic dose levels and therefore are advantageous as compared with depressant anti-epileptics such as phenobarbitone.

Accordingly, the present invention provides a compound of formula (III):

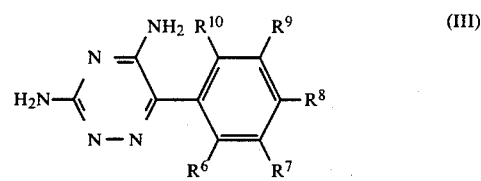

or an acid addition salt thereof, wherein $R^6$, $R^7$, $R^9$ and $R^{10}$ are each hydrogen, halogen, $C_{1-4}$ alkyl or trifluoromethyl and $R^8$ is chlorine or $R^7$ and $R^8$ are linked to form a —CH=CH—CH=CH— group when one of $R^6$ and $R^{10}$ is other than hydrogen provided that when $R^8$ is chlorine $R^6$, $R^7$, $R^9$ and $R^{10}$ are not all hydrogen atoms and that any one of $R^6$, $R^7$, $R^9$ and $R^{10}$ is not chlorine when the other three groups are hydrogen.

Suitably $R^6$, $R^7$, $R^9$ and $R^{10}$ are each hydrogen, chlorine, trifluoromethyl or methyl.

Preferred compounds of the formula (III) include:
3,5-diamino-6-(4-chloro-2-methylphenyl)-1,2,4-triazine
3,5-diamino-6-(4-chloro-3-trifluoromethylphenyl)-1,2,4-triazine.
3,5-diamino-6-(3-chloro-2-naphthyl)-1,2,4-triazine.

The present invention also provides the first practicable medical use of the compounds of the formula (III), as hereinbefore defined. Preferably this will be for the treatment of CNS disorders, and in particular epilepsy, in humans.

Suitable acid addition salts of the compounds of formula (III) include those formed with both organic and inorganic acids. Such acid addition salts will normally be pharmaceutically acceptable. Thus, preferred salts include those formed from hydrohloric, sulphuric, citric, tartaric, phosphoric, lactic, pyruvic, acetic, succinic, fumaric, maleic and oxaloacetic acids.

In a further aspect, the present invention provides pharmaceutical compositions comprising a compound of formula (III) in admixture with a pharmaceutically acceptable carrier. The compounds of the formula (III) will be present in the compositions of the present invention in an effective unit dosage form, that is to say in an amount sufficient to be effective against the CNS disorder in vivo.

The pharmaceutically acceptable carriers present in the compositions of the present invention are materials recommended for the purpose of administering the medicament. These may be liquid, solid or gaseous materials, which are otherwise inert or medically acceptable and are compatible with the active ingredients.

These pharmaceutical compositions may be given parenterally, orally, used as a suppository, or applied topically as an ointment, cream or powder. However, oral and parenteral administration of the compositions is preferred.

For oral administration, fine powders or granules will contain diluting, dispersing and/or surface active agents, and may be presented in a draught, in water or in a syrup, in capsules or sachets in the dry state or in a non-aqueous suspension wherein suspending agents may be included, or in a suspension in water or syrup. Where desirable or necessary, flavouring, preserving, suspending thickening or emulsifying agents can be included. When a suspension is prepared in water according to the present invention at least one of such agents will be present.

For parenteral administration, the compounds may be presented in sterile aqueous injection solutions which may contain anti-oxidants or buffers.

As stated above, free base or a salt thereof may be administrated in its pure form unassociated with other additives in which case a capsule or sachet is the preferred carrier.

Alternatively the active compound may be presented in a pure form as an effective unit dosage, for instance, compressed as a tablet or the like.

Other compounds which may be included are, for example, medically inert ingredients, e.g. solid and liquid diluents such as lactose, starch, or calcium phosphate for tablet or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessary ingredients such as humectants, preservatives, buffers, and antioxidants which are useful as carriers in such formulations.

Tablets or other forms of presentation provided in discrete units may conveniently contain an amount of compound of the formula (III) which is effective at such dosage or as a multiple of the same, for instance, units containing 5 mg to 500 mg., usually around 10 mg. to 250 mg.

The pharmaceutical compositions of the present invention will be prepared by the admixture of a compound of formula (III) with a pharmaceutically acceptable carrier. Conventional pharmaceutical excipients may be admixed as required.

The present invention provides a method of treatment of convulsions, particularly epilepsy, in mammals by the administration of a non-toxic anticonvulsant effective amount of a compound of the formula (III) or a pharmaceutically acceptable salt, or a composition as hereinbefore defined.

As indicated above, the compounds of the formula (III) are generally useful in treating such disorders by oral administration or injection.

The compounds of the formula (III) are normally administered at a dose of from 0.1 mg/kg. to 30 mg/kg. per day and conveniently 2 mg/kg per day. The dose range for adult humans is generally from 8 mg. to 2400 mg/day, preferably 35 to 1050 mg/day and conveniently 150 mg/day. Due to the fact that the compounds of the formula (III) are extremely long acting, it may often be advantageous to administer an initial dose of 70 to 2400 mg. the first day then a lower dose of 20 to 1200 mg. on subsequent days.

The present invention also provides a process for the preparation of compounds of the formula (III) which comprises the cyclisation of a compound of the formula (IV):

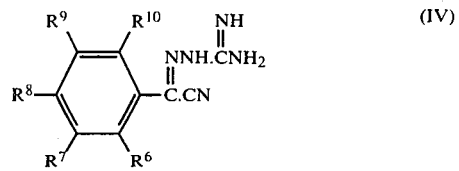

wherein $R^6$ to $R^9$ are as hereinbefore defined. This cyclisation reaction is normally carried out by refluxing in an alkanol, preferably a $C_{1-4}$ alkanol such as methanol or ethanol, in the presence of a strong base, such as potassium hydroxide.

The compounds of the formula (IV) are novel intermediates and as such form a further important part of the present invention.

The following examples illustrate the preparation of the compounds of the invention and their CNS activity.

EXAMPLE 1

Preparation of 3,5-diamino-6-(4-chloro-3-trifluoromethylphenyl)-1,2,4-triazine

A mixture of 4-chloro-3-trifluoromethylbenzoic acid (7.13 g, 32.2 mM) and thionyl chloride (20 ml) was heated to reflux for 2 hr. then evaporated down in vacuo to give the acid chloride as a clear oil. A solution of the above oil in dry xylene (10 ml) was added to a stirred mixture of cuprous cyanide (5.76 g, 64.6 mM) and finely ground potassium iodide (10.69 g, 64.6 mM) in xylene (100 ml), which had been dried by heating to reflux under a Dean and Stark trap for 16 hr. The resultant mixture was stirred and heated to reflux for 72 hr then cooled, filtered and the filtrate evaporated down in vacuo to give the crude aroyl cyanide as an oil, yield 5.76 g.

A solution of 4-chloro-3-trifluoromethylbenzoyl cyanide (5.76 g, 24.67 mM) in dimethyl sulphoxide (12 ml) was added dropwise to a stirred solution obtained after aminoguanidine bicarbonate (6.7 g, 94.3 mM) had been treated with 8N nitric acid (90 ml), so that the temperature remained at 20°-25° C. The resultant mixture was left at 20°-25° C. for 6 days then basified with 0.880 ammonia at a temperature not exceeding 25° C. The remaining solid was separated, washed thoroughly with water then dried.

The dry solid was added to a 10% solution of potassium hydroxide in methanol (50 ml) which was then heated to reflux for 1 hr. The resulting solution was evaporated down in vacuo and the residual solid was treated with ice water (100 ml). After a period of stirring (1 hr) the precipitated solid was isolated and dried. Subsequent recrystallisation from methylated spirits gave 3,5-diamino-6-(4-chloro-3-trifluoromethylphenyl)-1,2,4-triazine as an off-white powder, yield 1.34 g (14%), m.p. 228°-229° C. (uncorrected).

EXAMPLE 2

Using a method strictly analogous to that described in Example 1; 3,5-diamino-6-(4-chloro-2-methylphenyl)-1,2,4-triazine was prepared, yield 11.5% m.p. 183°-185° C. (uncorrected) and 3,5-diamino-6-(3-chloro-2-naphthyl)-1,2,4-triazine, yield 8.4% m.p. 263°-264° C. (uncorrected).

EXAMPLE 3

Pharmacological properties of the compounds of the present invention

The anticonvulsant activity of the compounds of the present invention was determined by a standard maximal electroshock test, that described by L. A. Woodbury and V. D. Davenport, *Arch. Int. Pharmacodyn.*, 1952, 92, 97.

| Compound | ED$_{50}$ mg/kg p.o. mice |
| --- | --- |
| 3,5-Diamino-6-(4-chloro-3-trifluoromethylphenyl)-1,2,4-triazine | 18.5 |
| 3,5-Diamino-6-(4-chloro-2-methylphenyl)-1,2,4-triazine | 14.8 |
| 3,5-Diamino-6-(3-chloro-2-naphthyl)-1,2,4-triazine | 12.0 |

| Tablet Formulation | | |
| --- | --- | --- |
| 3,5-Diamino-6-(3-chloro-2-naphthyl)-1,2,4,-triazine | 150 mg | |
| Lactose | 200 mg | contents per tablet |
| Maize Starch | 50 mg | |
| Polyvinylpyrrolidone | 4 mg | |
| Magnesium Stearate | 4 mg | |

The drug was mixed with the lactose and starch and granulated with a solution of the polyvinylpyrrolidone in water. The resultant granules were dried, mixed with magnesium stearate and compressed to give tablets of average weight 408 mg.

We claim:

1. 3,5-Diamino-6-(3-chloro-2-naphthyl)-1,2,4-triazine.

2. A pharmaceutically acceptable salt of 3,5-Diamino-6-(3-chloro-2-naphthyl)-1,2,4-triazine.

3. A compound of the formula

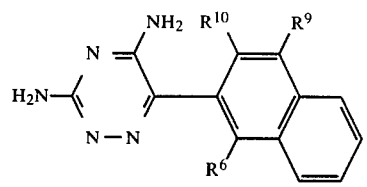

or a pharmaceutically acceptable acid addition salt thereof wherein $R^6$, $R^9$ and $R^{10}$ are each hydrogen, halogen, $C_{1-4}$ alkyl or trifluoromethyl with the proviso that one of $R^6$ and $R^{10}$ is other than hydrogen.

4. A pharmaceutical composition comprising the compound of claim 1 together with a pharmaceutically carrier.

5. A pharmaceutical composition comprising the salt of claim 2 together with a pharmaceutically carrier.

6. A pharmaceutical composition comprising the compound or salt of claim 3 together with a pharmaceutically acceptable carrier.

7. A method of treating convulsions in a mammal in need thereof comprising the administration of a non-toxic anticonvulsant effective amount of the compound of claim 1.

8. A method of treating convulsions in a mammal in need thereof comprising the administration of a non-toxic anticonvulsant effective amount of the salt of claim 2.

9. A method of treating convulsions in a mammal in need thereof comprising the administration of a non-toxic anticonvulsant effective amount of the compound or salt of claim 3.